United States Patent
Tamai et al.

(10) Patent No.: US 8,131,050 B2
(45) Date of Patent: Mar. 6, 2012

(54) RADIOGRAPHIC IMAGE CAPTURING APPARATUS AND RADIOGRAPHIC IMAGE CAPTURING METHOD

(75) Inventors: Shunichi Tamai, Chiba (JP); Takashi Yoshida, Yokosuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 769 days.

(21) Appl. No.: 12/269,226

(22) Filed: Nov. 12, 2008

(65) Prior Publication Data

US 2009/0123051 A1    May 14, 2009

(30) Foreign Application Priority Data

Nov. 14, 2007    (JP) .................................. 2007-296034

(51) Int. Cl.
*G06K 9/00*    (2006.01)

(52) U.S. Cl. ...................................................... 382/132

(58) Field of Classification Search .................. 382/128, 382/132
See application file for complete search history.

(56) References Cited

FOREIGN PATENT DOCUMENTS

| JP | 05-192319 A | 8/1993 |
| JP | 2003-290184 A | 10/2003 |

*Primary Examiner* — Jurie Yun
(74) *Attorney, Agent, or Firm* — Canon USA, Inc., I.P. Division

(57) ABSTRACT

The continuous image capturing of a subject is performed with small doses of radiation. A plurality of auxiliary images obtained by the continuous image capturing is stored. On the basis of the stored auxiliary images, the periodicity of motion of the subject is detected. A pseudo image is generated from the auxiliary images exhibiting the detected periodicity. The generated pseudo image is analyzed. On the basis of the analysis result, an image capturing parameter used for the main image capturing of a still image of the subject is calculated. Using the calculated image capturing parameter, the main image capturing of the still image of the subject is performed.

6 Claims, 5 Drawing Sheets

RADIOGRAPHIC IMAGE CAPTURING APPARATUS AND RADIOGRAPHIC IMAGE CAPTURING METHOD

BACKGROUND OF THE INVENTION

1. Field of the Invention

The present invention relates to a radiographic image capturing apparatus and a radiographic image capturing method for performing radiation image capturing.

2. Description of the Related Art

In recent years, medical radiographic image capturing apparatuses have generated digital images instead of analog images for use in diagnosing. Such a medical radiographic image capturing apparatus continuously captures radiographic digital images, and displays them on a monitor as a moving image or stores them in a memory or a hard disk. These captured radiographic digital images are used for diagnosing. A user of such a medical radiographic image capturing apparatus can obtain a still image useful for a diagnostic workup in such a manner that the user increases the dose of radiation in a desired scene while observing a moving image displayed on a monitor. The captured still image is stored in a memory or a hard disk.

In radiographic image capturing apparatuses, it is generally required to optimally set image capturing parameters (a radiation control variable, a device control variable, an image processing variable, etc.) so that still images useful for diagnosing can be obtained. An empirical value is usually derived on the basis of information about a part of a subject and is then set as an image capturing parameter. In some cases, an image pre-captured prior to main image capturing is analyzed, and an image capturing parameter is calculated and set on the basis of the analysis result.

On the other hand, in a case in which the image of a periodically moving subject such as lungs or a heart is captured, it is required to capture the image thereof at an optimum time for diagnosing. For example, the image of a human lung field can be captured at a desired time and in a desired condition (breath holding at the end of inhalation) under instructions from a radiographer or an operator. However, if the image of a heart, an unconscious patient (person), an animal, or a non-living material such as a machine is captured, it is difficult to perform image capturing at an optimum time. For example, Japanese Patent Laid-Open No. 2003-290184 discloses a technique used for human chest diagnosing in which a lung inflation cycle is detected and the main image capturing of a still image of lungs is performed on the basis of the detection result.

In the above-described image capturing, the reduction in the dose of radiation applied to a subject is needed. More specifically, Japanese Patent Laid-Open No. 5-192319 discloses a technique for obtaining a diagnostic image with small doses of radiation by detecting the change in a subject using captured images to be used for diagnosing and changing a frame rate or the dose of radiation on the basis of the detection result.

However, since experience is required to optimally set an image capturing parameter used for the main image capturing of a still image, it is difficult for unskilled users to obtain an image useful for diagnosing.

If the above-described method of analyzing pre-captured images and setting an effective radiation control parameter on the basis of the analysis result is used, it is required to use images pre-captured with the same irradiation dose as for the main image capturing or an irradiation dose that is lower than that for the main image capturing but is still relatively high. Accordingly, the reduction in the dose of radiation applied to a subject cannot be achieved.

SUMMARY OF THE INVENTION

The present invention provides a radiographic image capturing apparatus and a radiographic image capturing method capable of calculating an appropriate image capturing parameter used for the main image capturing of a still image of a subject on the basis of a plurality of auxiliary images that have been continuously captured with small doses of radiation.

According to an aspect of the present invention, a radiographic image capturing apparatus includes: an auxiliary image capturing unit configured to continuously capture a plurality of images of a subject with small doses of radiation; a storage unit configured to store the images captured by the auxiliary image capturing unit as a plurality of auxiliary images; a detection unit configured to detect periodicity of motion of the subject based on the auxiliary images; a generation unit configured to generate a pseudo image from those auxiliary images exhibiting the detected periodicity; a calculation unit configured to analyze the generated pseudo image and, based on an analysis result, calculate an image capturing parameter used for main image capturing of a still image of the subject; and a main image capturing unit configured to perform the main image capturing of the still image of the subject using the image capturing parameter.

According to another aspect of the present invention, a radiographic image capturing method includes: continuously capturing a plurality of images of a subject with small doses of radiation; storing the captured images as a plurality of auxiliary images; detecting periodicity of motion of the subject based on the auxiliary images; generating a pseudo image from those auxiliary images exhibiting the detected periodicity; analyzing the generated pseudo image and, based on an analysis result, calculating an image capturing parameter used for main image capturing of a still image of the subject; and performing the main image capturing of the still image of the subject using the image capturing parameter.

According to another aspect of the present invention, a radiation image capturing apparatus includes: a control unit configured to control radiation image capturing of a moving subject, wherein motion of the moving subject has a periodic component; and an acquisition unit configured to acquire a radiographic images obtained by the radiation image capturing. The control unit performs continuous radiation image capturing with a first irradiation dose, specifies periodicity of motion of the subject based on a plurality of radiographic images obtained by the continuous radiation image capturing and acquired by the acquisition unit, and determines timing of radiation image capturing performed with a second irradiation dose larger than the first irradiation dose.

Further features of the present invention will become apparent from the following description of exemplary embodiments with reference to the attached drawings.

DESCRIPTION OF THE EMBODIMENTS

Embodiments of the present invention will be described in detail with reference to the accompanying drawings.

Figure 1:
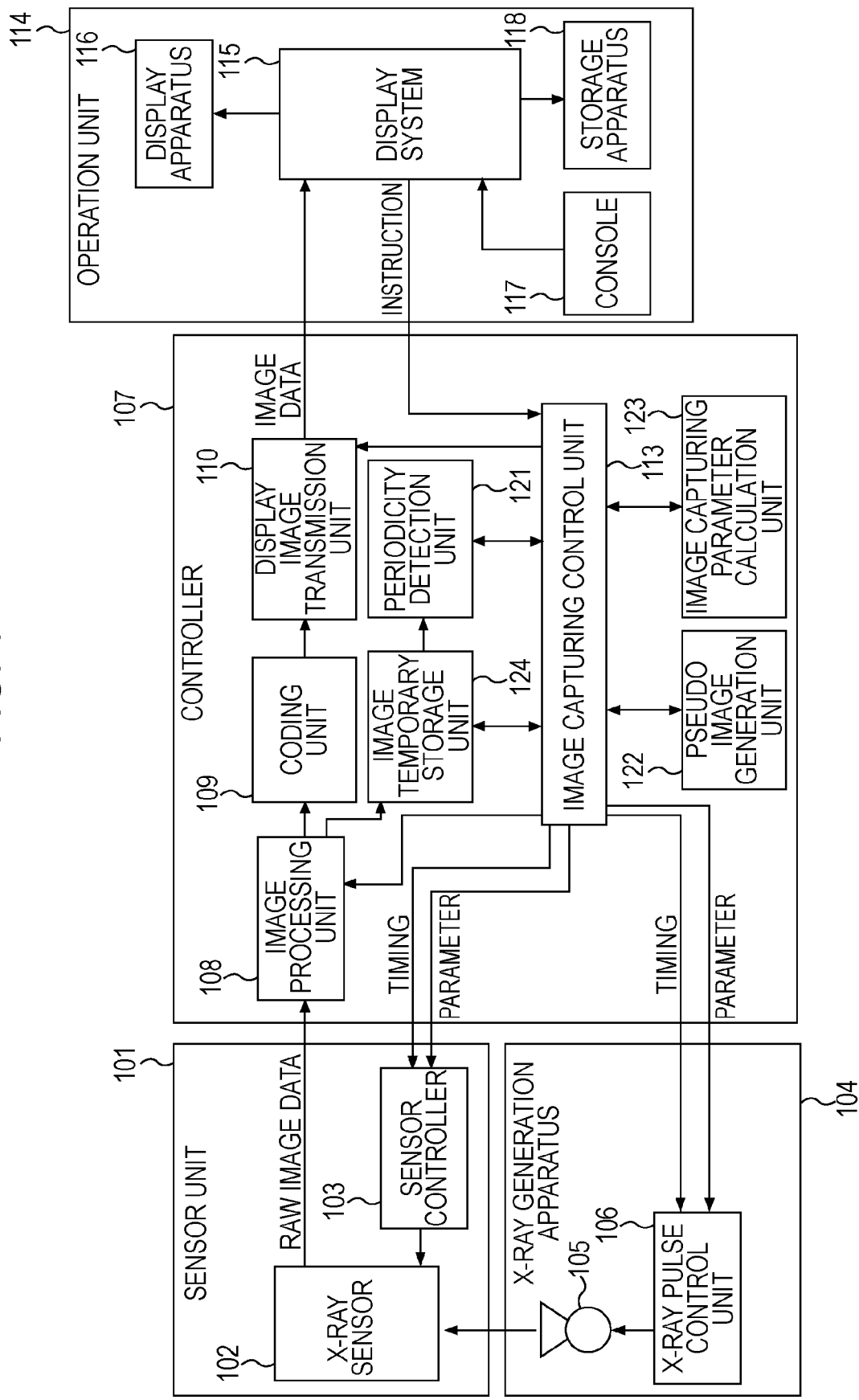
FIG. 1 is a block diagram illustrating the configuration of a radiographic image capturing apparatus according to an embodiment of the present invention.

FIG. 1 is a block diagram illustrating the configuration of a radiographic image capturing apparatus according to an embodiment of the present invention.

As illustrated in FIG. 1, a radiographic image capturing apparatus includes a sensor unit 101, an X-ray generation apparatus 104, a controller 107, and an operation unit 114.

The sensor unit 101 includes an X-ray sensor 102 and a sensor controller 103. The X-ray sensor 102 includes a solid-state image pickup element for reacting with an X-ray, converting the detected X-ray into an electric signal in accordance with the intensity of the X-ray, and outputting the electric signal. Alternatively, the X-ray sensor 102 includes a fluorescent member for emitting fluorescent light in accordance with the energy of an X-ray and a photoelectric conversion element for converting the visible light into an electric signal in accordance with the intensity of the visible light. The X-ray sensor 102 may be a unit including a solid-state image pickup element and a photoelectric conversion element. Raw image digital data output from the sensor unit 101 is transmitted to the controller 107.

The sensor controller 103 performs pieces of sensor drive control processing such as processing for generating a data output timing signal for the X-ray sensor 102 in response to a timing instruction transmitted from an image capturing control unit 113 and processing for setting a sensor output mode. The description of the timing instruction will be made later.

A high-speed digital interface such as an LVDS (Low Voltage Differential Signaling) interface is used as a data transfer interface between the sensor unit 101 and the controller 107. An asynchronous serial communication interface such as a UART interface is used as a parameter input/output interface between the sensor unit 101 and the controller 107.

The X-ray generation apparatus 104 includes an X-ray tube 105 and an X-ray pulse control unit 106. The X-ray tube 105 emits a pulsed X-ray in response to a timing signal transmitted from the X-ray pulse control unit 106. The X-ray pulse control unit 106 performs timing signal output control processing in response to a timing instruction or a setting parameter transmitted from the image capturing control unit 113 so that an X-ray irradiation timing signal is output to the X-ray tube 105 under a predetermined irradiation condition.

The controller 107 includes an image processing unit 108, a coding unit 109, a display image transmission unit 110, a periodicity detection unit 121, a pseudo image generation unit 122, an image capturing parameter calculation unit 123, an image temporary storage unit 124, and an image capturing control unit 113.

A low-latency network protocol such as an asynchronous serial communication protocol or a CAN (Controller Area Network) protocol is used a parameter input/output protocol between the X-ray generation apparatus 104 and the controller 107.

The image capturing control unit 113 included in the controller 107 continuously transmits timing instructions to the X-ray generation apparatus 104 and the sensor unit 101, thereby enabling the continuous image capturing of X-ray radioscopic images. For example, by transmitting a timing instruction 30 times per second, moving image data of 30 frames/sec can be generated.

Upon receiving the raw image digital data output from the sensor unit 101, the image processing unit 108 performs predetermined pieces of image processing including correction and noise reduction which are performed in accordance with the characteristic of the X-ray sensor 102 and high-quality image processing such as dynamic range improvement.

The image processing unit 108 transmits to the image temporary storage unit 124 data of an auxiliary image captured for use in periodicity detection and transmits to the coding unit 109 only data of an image captured for use in diagnosing, that is, display image data.

The coding unit 109 performs lossless coding upon the display image data, and transmits the processed display image data to the display image transmission unit 110. The controller 107 and the operation unit 114 are connected to each other via a Gigabit Ethernet® network. The display image transmission unit 110 performs image data packetization and network protocol processing upon the display image data, and transmits the processed display image data to the operation unit 114.

In response to an instruction transmitted from the image capturing control unit 113, the image temporary storage unit 124 stores in a temporal storage apparatus (not illustrated) the auxiliary image captured for use in periodicity detection and pieces of information about an image capturing time, a serial number, and a label. In this embodiment, this temporal storage apparatus uses a memory included in the controller 107. However, any storage medium capable of temporarily storing data may be used.

The periodicity detection unit 121 calculates the amount of motion of a subject using a plurality of auxiliary images stored in the image temporary storage unit 124, and detects the periodicity of the motion of the subject on the basis of the amount of motion. Furthermore, the periodicity detection unit 121 calculates the time of a predetermined phase and a still image capturing time on the basis of a cycle exhibiting the detected periodicity.

A motion detection algorithm such as an optical flow is widely used as a technique in the related art, and the description thereof will be therefore omitted. More specifically, examples of the motion detection algorithm include a spatio-temporal gradient method, a correlation method based on correlation calculation, and a block matching method (template matching method). In this embodiment, using the detected amount of change in motion, periodicity is detected.

The pseudo image generation unit 122 acquires corresponding auxiliary images from the image temporary storage unit 124 on the basis of the time of the predetermined phase calculated by the periodicity detection unit 121, and adds these auxiliary images so as to generate a pseudo image in the image temporary storage unit 124.

The image capturing parameter calculation unit 123 analyzes the pseudo image generated by the pseudo image generation unit 122 so as to calculate an image capturing parameter used for the main image capturing of a still image. Examples of the image capturing parameter include a tube current, a tube voltage, and an irradiation period which are used for controlling X-ray irradiation, an analog amplifier gain value used for controlling a sensor device, a gain characteristic used for image processing, and a gamma characteristic.

The image capturing control unit 113 transmits an image capturing timing instruction and a parameter to the sensor unit 101, the X-ray generation apparatus 104, and the image processing unit 108 using a predetermined auxiliary image capturing parameter at the time of periodicity detection. Furthermore, the image capturing control unit 113 controls the sensor unit 101, the X-ray generation apparatus 104, and the image processing unit 108 using the image capturing parameter calculated by the image capturing parameter calculation unit 123 at the time of the main capturing of a still image.

Still furthermore, the image capturing control unit 113 transmits a parameter instruction to the sensor unit 101, the X-ray generation apparatus 104, and the image processing unit 108 on the basis of an image capturing condition transmitted from the operation unit 114. The image capturing control unit 113 includes a CPU and computer-readable storage media such as a RAM and a ROM storing a program for executing a flowchart illustrated in FIG. 2.

The operation unit 114 includes a display system 115, a display apparatus 116, a console 117, and a storage apparatus 118. The operation unit 114 is composed of a PC (Personal Computer) and peripherals connected to the PC. The display system 115 is implemented by the PC and application software running on the PC. The display system 115 receives coded image data transmitted from the controller 107 via the network, decodes the image data, and performs the output of the image data to the display apparatus 116 or the storage of the image data in the storage apparatus 118. Furthermore, in response to an instruction input transmitted from the console 117, the display system 115 transmits various instructions, for example, an image capturing start/stop instruction and an image capturing mode setting instruction, to the controller 107 via the network.

In this embodiment, the auxiliary images captured for use in periodicity detection are stored in the image temporary storage unit 124. However, like the still image that is obtained for use in diagnosing by the main image capturing, these auxiliary images may be transmitted to the display system 115 via the coding unit 109, and then be displayed on the display apparatus 116 or stored in the storage apparatus 118 as pieces of image data.

Next, a control process performed by the image capturing control unit 113 included in the controller 107 illustrated in FIG. 1 will be described with reference to FIG. 2.

Figure 2:
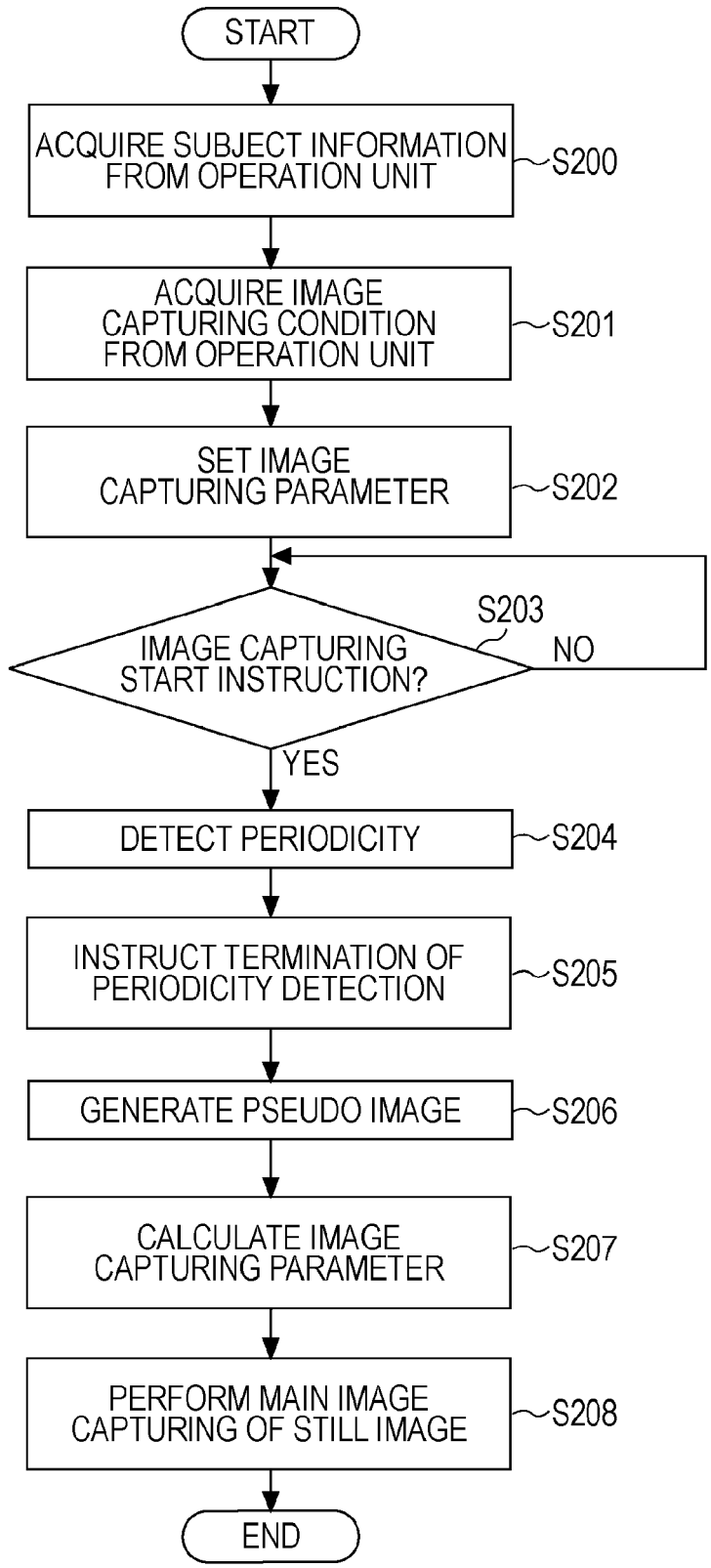
FIG. 2 is a flowchart illustrating a control process performed by an image capturing control unit illustrated in FIG. 1.

FIG. 2 is flowchart illustrating the control process performed by the image capturing control unit 113 illustrated in FIG. 1. First, in step S200, the image capturing control unit 113 receives information about a subject (subject information) from the operation unit 114. More specifically, a user inputs the subject information using an input screen (not illustrated) that is displayed on the display apparatus 116 by application software running on the display system 115. The subject information includes the type of a subject (human, dog, cat, etc.), the name of an image capturing area (lung, diaphragm, heart, etc.), and subject unique information (the thickness, size, and gender of the subject, etc.).

The image capturing control unit 113 sets the default values for a parameter used for the image capturing of an auxiliary image for use in periodicity detection, a parameter used for the main image capturing of a still image, and a focused phase in the main image capturing. These default values are prepared as pieces of data of application software, and empirical values or experimental values are employed as the default values. However, the default values are not limited thereto. A table used to change an image capturing parameter in accordance with an input value of the unique information such as thickness information is prepared. Using the table, a default value is set. The relationship between an input value and an image capturing parameter may be calculated using a function.

Next, in step S201, the image capturing control unit 113 acquires from the operation unit 114 the image capturing parameter used for periodicity detection and information about an initial condition such as a method used for periodicity detection. The image capturing parameter used for periodicity detection is not necessarily a parameter for achieving a high-quality diagnostic image, and may be a parameter for achieving an image of quality enabling the detection of subject motion while minimizing an X-ray irradiation dose.

Figure 3:
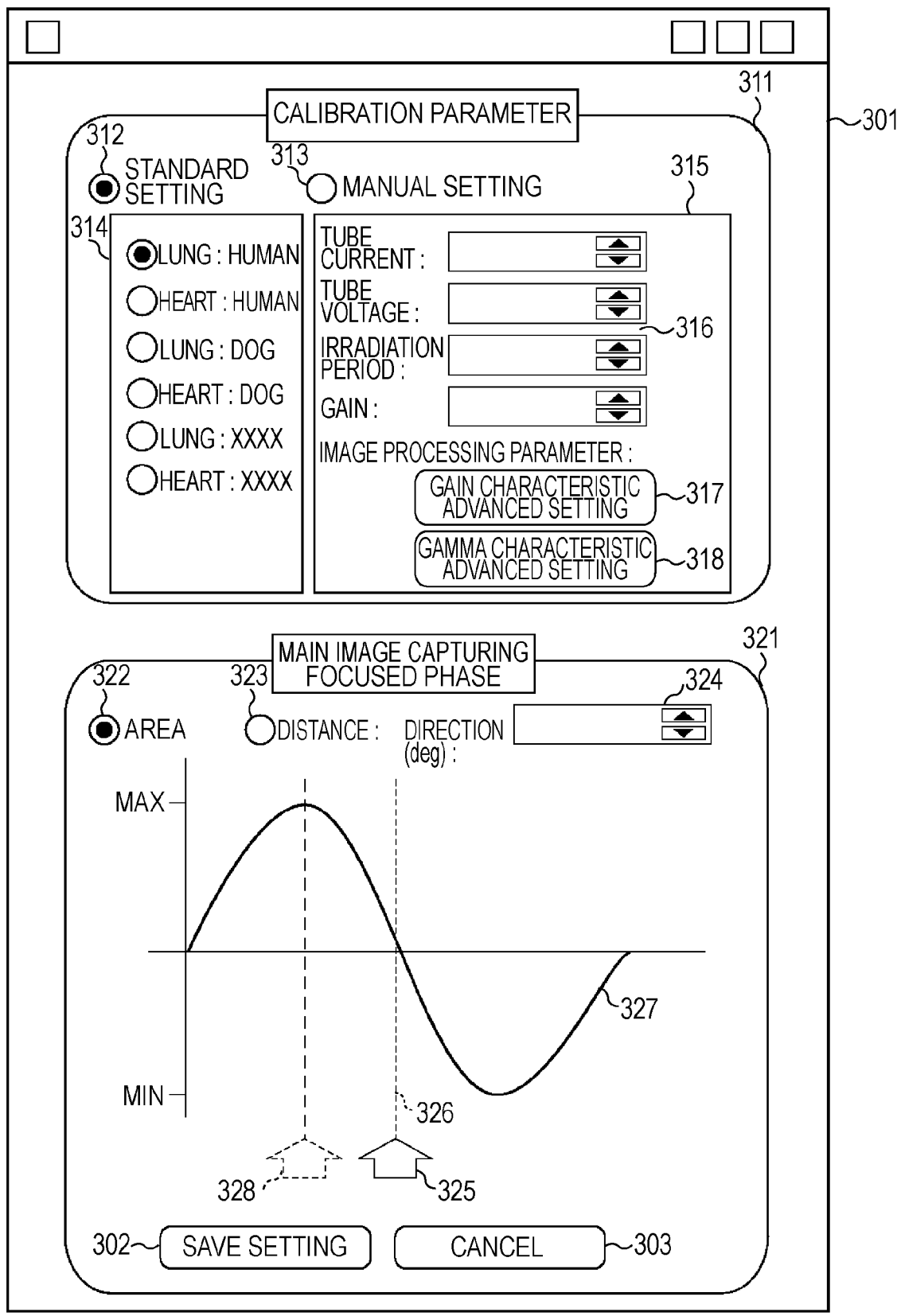
FIG. 3 is a diagram illustrating an example of a parameter input screen according to an embodiment of the present invention.

In this embodiment, an input screen 301 illustrated in FIG. 3 is used in which there are two parameter setting methods one of which allows a user to select one of sets of representative subject parameters (human lung field, human heart, etc.) as an image capturing parameter used for periodicity detection and the other one of which allows an expert to individually set parameters.

FIG. 3 is a diagram illustrating an example of a parameter input screen according to an embodiment of the present invention. Referring to FIG. 3, in an area 311 used to set X-ray image capturing parameters used for the image capturing of auxiliary images for use in periodicity detection, a user can select one of a standard setting 312 and a manual setting 313. In an initial state, a standard setting item corresponding to the subject information input in step S200 is selected and displayed. Another item may be selected from among candidates included in an area 314. The list of these candidates is merely illustrative, and another list may therefore be used.

On the other hand, if the user selects the manual setting 313, the user can set specific image capturing parameters included in an area 315. For example, the user can set X-ray control parameters such as a tube current, a tube voltage, and an irradiation period and a device control parameter such as an amplifier gain value as denoted by a numeral 316. In the case of the setting of image processing parameters, by pressing a gain characteristic advanced setting button 317 or a gamma characteristic advanced setting button 318, another window (not illustrated) is displayed and the user can perform advanced setting on the displayed window. Items that can be set as image capturing parameters are not limited to the above-described items. More detailed items may be displayed on the input screen, or a simplified input screen may be used.

An area 321 is used to set a main image capturing time using a phase. First, information used for periodicity detection is selected. If the change in the area of a target part of a subject is used as the periodicity detection information, an item of area 322 is selected. If the change in distance in a specific direction is used as the periodicity detection information, an item of distance 323 is selected and the specific direction is set in an area 324.

A curve 327 graphically represents the change in one cycle. In the graph, the horizontal axis denotes time and the vertical axis denotes area when the item of area 322 is selected as the periodicity detection information or distance when the item of distance 323 is selected as the periodicity detection information. Such an interface is employed in which by dragging an arrow icon 325 left and right with a mouse, an auxiliary line 326 is moved left and right in synchronization with the arrow icon 325. By releasing the pressing of a mouse button at a desired position, a desired phase can be specified. For example, if human lungs are diagnosed, image capturing is often performed when the lungs are inflated by inhalation. In this case, a position 328 at which the maximum area of the lungs can be obtained (a phase in which the maximum amplitude can be obtained) is specified.

By pressing a setting save button 302, the setting of X-ray image capturing parameters used for the image capturing of auxiliary images at the time of periodicity detection is saved. On the other hand, by pressing a cancel button 303, pieces of setting information specified on the input screen 301 are reset to the initial state.

Referring back to FIG. 2, in step S202, various image capturing parameters are set on the basis of the image capturing conditions acquired in step S201. More specifically, by transmitting setting parameter commands to the sensor controller 103, the X-ray pulse control unit 106, and the image processing unit 108, the setting of the X-ray irradiation dose, the setting of a sensor read mode, and the setting of an image processing parameter are performed. Next, in step S203, the image capturing control unit 113 waits until an image capturing start instruction is transmitted from the operation unit 114.

Figure 4:
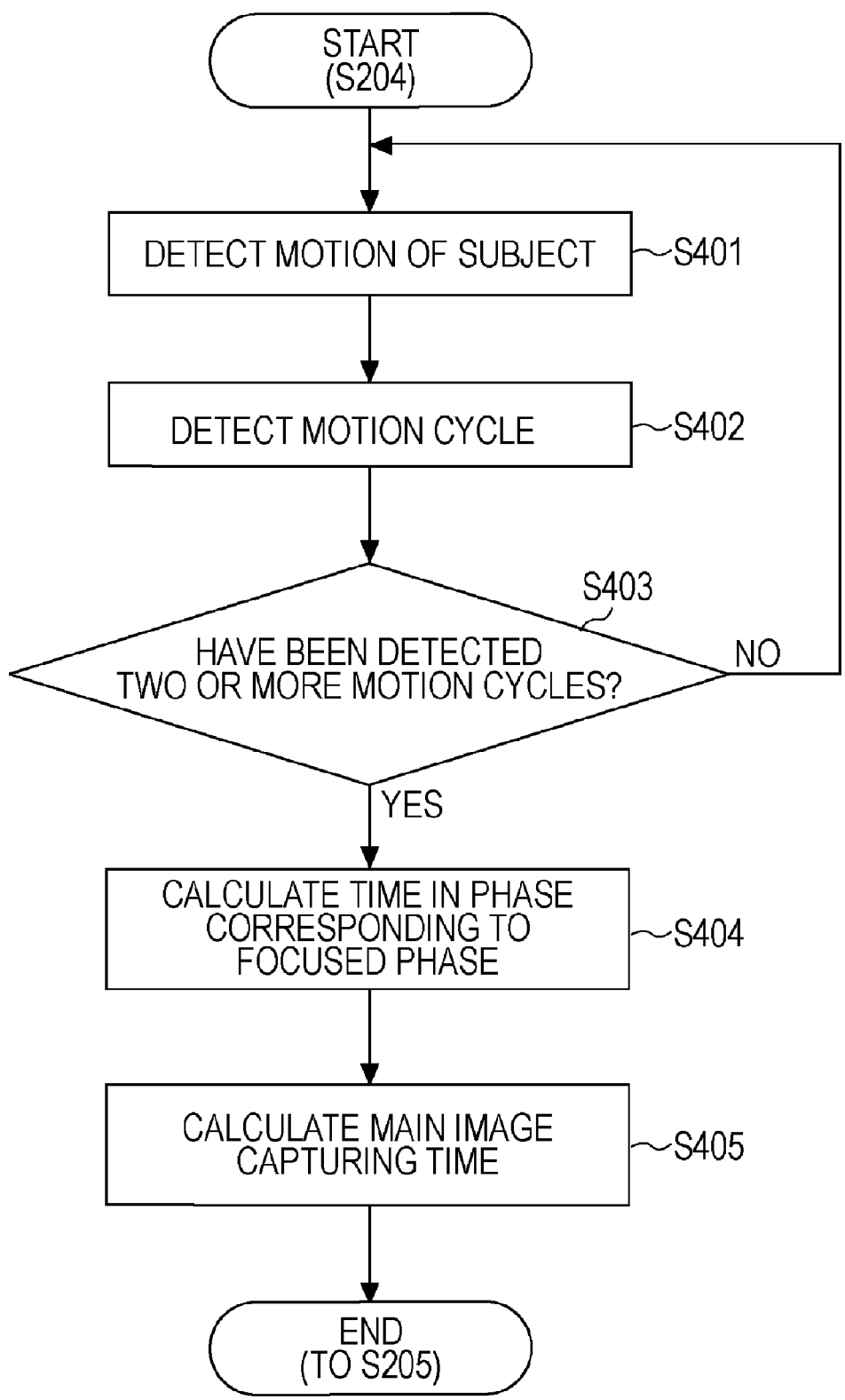
FIG. 4 is a flowchart illustrating the details of a periodicity detection process.

If the image capturing start instruction is transmitted from the operation unit 114, in step S204, the image capturing control unit 113 continuously captures the images of the subject so as to start the detection of periodicity of subject motion. The process performed in step S204 will be described in detail with reference to FIG. 4. FIG. 4 is a flowchart illustrating the details of the process performed in step S203 illustrated in FIG. 2. In step S401, the image capturing control unit 113 detects the motion of the subject. As described previously, a motion detection algorithm is well known, and the description thereof will be therefore omitted. Each time image capturing is performed, the amount of change in the motion of the subject is calculated using the auxiliary image obtained by the image capturing and the last captured auxiliary image. The calculated amount of change is stored in the image temporary storage unit 124 as auxiliary image information of the obtained auxiliary image along with information about the image capturing time.

Subsequently, in step S402, the cycle of the motion of the subject is detected. More specifically, by referring to the last five amounts of change in the motion of the subject, it is determined whether the motion change amount changes from plus to minus or minus to plus. If the motion change amount changes from plus to minus, one of the motion change amounts having the value closest to zero is set as the amplitude maximum value. If the motion change amount changes from minus to plus, one of the motion change amounts having the value closest to zero is set as the amplitude minimum value. Information about the amplitude maximum (minimum) value is added to corresponding auxiliary image information.

In step S403, it is determined whether two or more maximum values and two or more minimum values (the maximum and minimum values obtained in two cycles) have been obtained. If it is determined in step S403 that two or more maximum values and two or more minimum values have not yet been obtained, the process from step S401 to step S402 is repeated until they are obtained. This periodicity detection algorithm is not limited to the above-described method, and another method may be used.

In step S404, the time of a phase corresponding to the focused phase, which has been input in advance, is calculated using the pieces of auxiliary image information. In this embodiment, since two cycles are detected, the calculation of the time of the phase corresponding to the focused phase is performed two times. In this embodiment, a time position between the maximum value and the minimum value is calculated using a proportional expression. However, a calculation method is not limited thereto. Furthermore, in this embodiment, two cycles are detected. However, another method capable of achieving similar effects may be used.

In step S405, a main image capturing time is calculated. In this embodiment, using the obtained maximum values and the obtained minimum values which are included in the detected two cycles, the average of periods of time each elapsed between the maximum value and the minimum value is calculated. Using the calculated average period of time, the next maximum value occurrence time and the next minimum value occurrence time are estimated. On the basis of the estimation results, the next focused phase occurrence time is calculated and the calculation result is set as a main image capturing time. However, in view of the computing speed of a system, if the interval between the calculated main image capturing time and the current time is short, the time of occurrence of the focused phase in a cycle after the next cycle is set as the main image capturing time.

Referring back to the flowchart illustrated in FIG. 2, if the above-described periodicity detection is completed, in step S205, the image capturing control unit 113 transmits an instruction for terminating X-ray irradiation to the image capturing control unit 113 and the X-ray pulse control unit 106. Thus, the auxiliary image capturing is completed. At the same time, the image capturing control unit 113 transmits the list of the focused phase occurrence times calculated in the periodicity detection process to the pseudo image generation unit 122.

In step S206, a pseudo image is generated by adding all of the auxiliary images captured immediately before and after the focused phase occurrence times. The generated pseudo image is stored in the image temporary storage unit 124. In this embodiment, since the list of two calculated times is transmitted to the pseudo image generation unit 122, a total of four auxiliary images are added. However, the pseudo image generation method is not limited thereto.

In step S207, the image capturing control unit 113 instructs the image capturing parameter calculation unit 123 to analyze the pseudo image generated in step S206 and calculate an image capturing parameter used for the main image capturing of a still image on the basis of the analysis result. The image capturing parameter calculation unit 123 generates a density histogram as the feature value of the pseudo image, and calculates a main image capturing parameter on the basis of a density distribution, a main density region, and the image capturing parameter that has been used in the image capturing of the auxiliary images for use in the periodicity detection.

For example, if the density range of a target region of a subject is less than a predetermined value, a tube voltage is set to a value less than the default value of the tube voltage, which is one of main image capturing parameters, by one. By setting a lower tube voltage, the wavelength of an X-ray is increased and the penetrating power of the X-ray is weakened. As a result, the number of visible tissues is increased. In contrast, if the density range is larger than a predetermined value, a tube voltage is set to a value greater than the default value of the tube voltage by one. By setting a higher tube voltage, the contrast is increased.

In this embodiment, the default value of a main image capturing parameter is set on the basis of the subject information input in step S200. The image capturing control unit 113 has a table of the increments or decrements of an image feature value. As each of the increments or decrements, an empirical value or an experimental value is used. However, another type of value may be used. A method of calculating the relationship between an image feature value and an image capturing parameter using a function may be used.

Furthermore, in this embodiment, a density histogram is used as an image feature value. However, another method capable of calculating an appropriate image capturing parameter from the image feature value of a pseudo image may be used.

Subsequently, in step S208, the image capturing control unit 113 sets the image capturing parameter calculated in step S207 for the sensor controller 103, the X-ray pulse control unit 106, and the image processing unit 108, and performs the main image capturing of a still image at the main still image capturing time calculated in step S205. The captured image is transmitted to the display system 115 and is then displayed on the display apparatus 116. At the same time, the captured image is stored in the storage apparatus 118.

Here, the correlation among the X-ray irradiation dose, the irradiation time, and the periodicity detection in a period from the periodicity detection to the main image capturing will be described with reference to FIG. 5.

Figure 5:
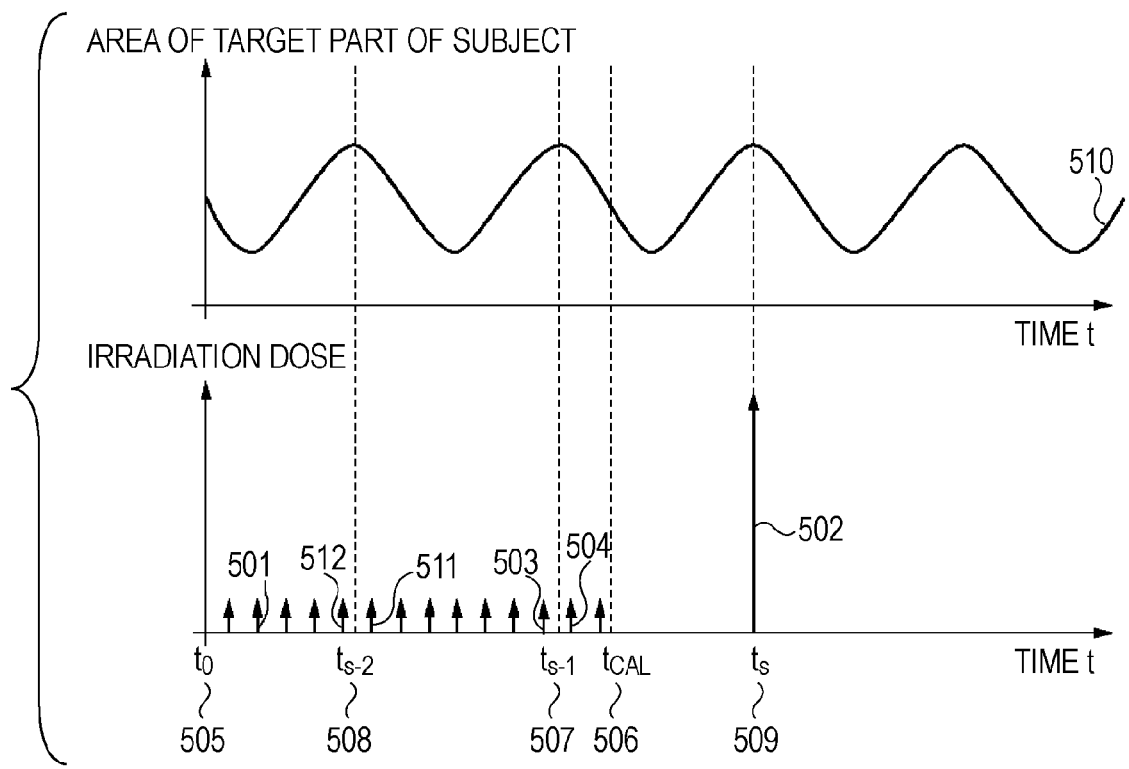
FIG. 5 is a diagram illustrating the correlation among an X-ray irradiation dose, an irradiation time, and periodicity detection in a period from periodicity detection to main image capturing.

FIG. 5 is a diagram illustrating the correlation among the X-ray irradiation dose, the irradiation time, and the periodicity detection in a period from the periodicity detection to the main image capturing. Referring to FIG. 5, the horizontal axes denote time, the vertical axis in the upper portion of the drawing denotes the area of a target part of a subject, and the vertical axis in the lower portion of the drawing denotes the X-ray irradiation dose. It is assumed that a point at which the maximum area of the periodically moving target part is obtained is set as the main image capturing time.

An arrow 501 denotes the X-ray irradiation dose in the periodicity detection (first irradiation dose). An arrow 502 denotes the X-ray irradiation dose in the main still image capturing (second irradiation dose). At a time t0 (505), the image capturing is started. Before the periodicity is detected, the image capturing of auxiliary images is performed with a very weak X-ray (501). The number of arrows illustrated in FIG. 5 corresponds to the number of times X-ray irradiation is performed, but is different from the actual number of times X-ray irradiation is performed.

The image capturing of auxiliary images is completed at a time tCAL (506) after the periodicity has been detected. In FIG. 5, the detected periodicity is illustrated by a curve 510 for the purpose of explaining features of the invention. However, it is not necessary to display such a curve to implement the invention. A period of time from the time t0 (505) to the time tCAL (506) is a period of time taken to detect the periodicity. Times tS-1 (507) and tS-2 (508) at which the focused phase is obtained and a main still image capturing time tS (509) are calculated.

A pseudo image used to calculate an image capturing parameter used for main image capturing is generated from auxiliary images captured immediately before and after the two times tS-1(507) and tS-2(508) at which the focused phase is obtained. That is, using images obtained by irradiation at times 503, 504, 511, and 512, a pseudo image is generated.

Figure 6:
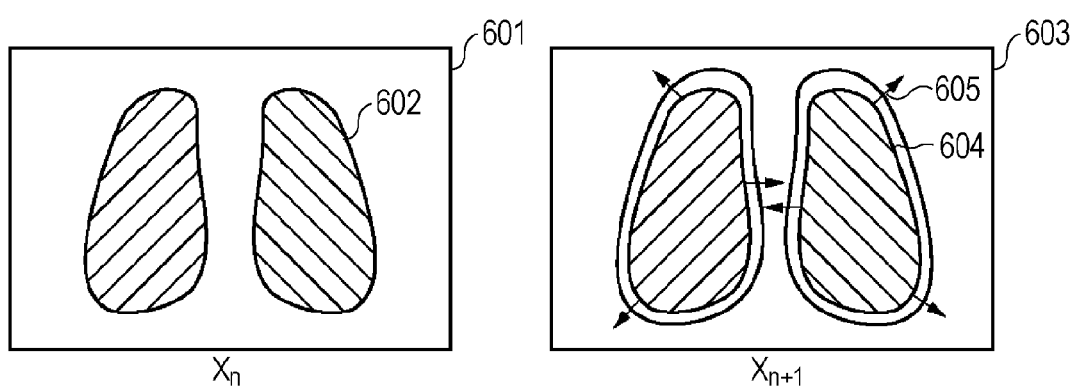
FIG. 6 is a diagram illustrating the captured images of a moving subject.

FIG. 6 is a diagram illustrating captured images of a moving subject. Referring to FIG. 6, an image 601 denotes an image captured in a certain frame (Xn), and an image 603 denotes an image captured in the next frame (Xn+1). The image 601 denotes the deflation state of lungs 602 serving as a subject in the frame (Xn). The image 603 denotes the transition from a deflation state 604 to an inflation state 605 of the lungs 602.

In the motion detection performed by the periodicity detection unit 121, for example, if a phase in which the maximum area of the subject is obtained is set as the focused phase, the sum total of detected vectors is calculated and the distance of the sum total of detected vectors is set as the amount of change. Using the amount of change, phase determination can be performed. In this example, if the amount of change changes from a positive value to zero, it is determined that the subject in an inhalation state (in this case, the maximum area of the subject is obtained when the value is zero). If the amount of change changes from zero to a negative value, and changes from the negative value back to zero, it is determined that the subject in an exhalation state (the minimum area of the subject is obtained when the value becomes zero again). If the amount of change changes from zero to a positive value, it is determined that the subject is in an inhalation state.

In this embodiment, the image capturing with a small dose of X-ray is performed in response to a user's instruction input from the operation unit 114. However, another method enabling the image capturing of auxiliary images with small doses of X-ray and the periodicity detection using the captured auxiliary images may be used. Furthermore, a periodicity detection method is not limited to the above-described method. Another method enabling the acquisition of a focused phase may be used.

According to this embodiment, the motion of a periodically moving subject is detected with small doses of radiation so as to detect the periodicity of the subject motion. An image capturing parameter allowing main image capturing using a desired phase is calculated from a pseudo image generated by adding auxiliary images captured for the periodicity detection. The main image capturing is performed using the image capturing parameter. Consequently, a high-resolution radiographic diagnostic image can be obtained with the minimum dose of radiation. Furthermore, by generating a pseudo image used for the calculation of a main image capturing parameter using a method of adding auxiliary images captured with small doses of radiation, it is not required to take the effects of particular noise and artifacts, which are prone to occur at the time of image capturing with a small dose of radiation, into consideration.

A storage medium storing the program code of software capable of achieving the functions of the above-described embodiments may be used. In this case, the storage medium is supplied to a system or an apparatus. The computer (CPU or MPU) of the system or apparatus reads out the program code from the storage medium and executes the read program code, whereby the functions of the above-described embodiments can be achieved.

In this case, the program code read out from the computer-readable storage medium and executed by the computer achieves the functions of the above-described embodiments. Program code for implementing the present invention stored in a computer readable medium is an embodiment of the present invention.

The storage medium used to supply the program code may be a flexible disk, a hard disk, an optical disc, a magneto-optical disk, a CD-ROM, a CD-R, a magnetic tape, a non-volatile memory card, or a ROM.

As described previously, the computer executes the read program code, whereby the functions of the above-described embodiments are achieved. In addition to this case, the functions of the above-described embodiments are also achieved in a case in which an OS (operating system) or the like running on the computer performs a part of or all of the processing in response to the instructions of the program code.

Furthermore, the program code read out from the storage medium may be written in the memory of a function expansion board inserted into the computer or a function expansion unit connected to the computer. In this case, a CPU included in the function expansion board or the function expansion unit performs a part of or all of the processing in response to the instructions of the program code, whereby the functions of the above-described embodiments are achieved.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2007-296034 filed Nov. 14, 2007, which is hereby incorporated by reference herein in its entirety.

What is claimed is:

1. A radiographic image capturing apparatus comprising:
an auxiliary image capturing unit configured to continuously capture a plurality of images of a subject with small doses of radiation;
a storage unit configured to store the images captured by the auxiliary image capturing unit as a plurality of auxiliary images;
a detection unit configured to detect periodicity of motion of the subject based on the auxiliary images;
a generation unit configured to generate a pseudo image from those auxiliary images exhibiting the detected periodicity;
a calculation unit configured to analyze the generated pseudo image and, based on an analysis result, calculate an image capturing parameter used for main image capturing of a still image of the subject; and
a main image capturing unit configured to perform the main image capturing of the still image of the subject using the image capturing parameter.

2. The radiographic image capturing apparatus according to claim 1, further comprising an input unit configured to allow an operator to specify timing, relative to the detected periodicity, of the main image capturing of the still image of the subject, and
wherein the generation unit generates the pseudo image using ones of the auxiliary images which have been captured at the specified timing.

3. The radiographic image capturing apparatus according to claim 1, further comprising a main image capturing time calculation unit configured to calculate, based on the detected periodicity, a time at which the main image capturing of the still image of the subject is performed, and
wherein the main image capturing unit performs the main image capturing of a still image of the subject using the image capturing parameter at the calculated time.

4. A radiographic image capturing method comprising:
continuously capturing a plurality of images of a subject with small doses of radiation;
storing the captured images as a plurality of auxiliary images;
detecting periodicity of motion of the subject based on the auxiliary images;
generating a pseudo image from those auxiliary images exhibiting the detected periodicity;
analyzing the generated pseudo image and, based on an analysis result, calculating an image capturing parameter used for main image capturing of a still image of the subject; and
performing the main image capturing of the still image of the subject using the image capturing parameter.

5. A radiation image capturing apparatus comprising:
a control unit configured to control radiation image capturing of a moving subject, wherein motion of the moving subject has a periodic component; and
an acquisition unit configured to acquire radiographic images obtained by the radiation image capturing, and
wherein the control unit performs continuous radiation image capturing with a first irradiation dose, specifies periodicity of motion of the subject based on a plurality of radiographic images obtained by the continuous radiation image capturing and acquired by the acquisition unit, and determines timing of radiation image capturing performed with a second irradiation dose larger than the first irradiation dose.

6. The radiation image capturing apparatus according to claim 5, further comprising a determination unit configured to determine a parameter used for the radiation image capturing performed with the second irradiation dose based on ones of said plurality of radiographic images which have the same phase as a phase at the timing of the radiation image capturing performed with the second irradiation dose.

* * * * *